United States Patent
Takada (10) Patent No.: US 6,357,877 B2
(45) Date of Patent: Mar. 19, 2002

(54) OPHTHALMIC APPARATUS

(75) Inventor: Yasutoshi Takada, Gamagori (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 09/745,529

(22) Filed: Dec. 26, 2000

(30) Foreign Application Priority Data

Jan. 7, 2000 (JP) ............................................ 12-001314

(51) Int. Cl.[7] ................................................ A61B 3/10
(52) U.S. Cl. ..................................................... 351/221
(58) Field of Search ............................... 351/221, 237, 351/242; 606/4, 5, 10, 11

(56) References Cited

U.S. PATENT DOCUMENTS

| | | |
|---|---|---|
| 3,760,174 A | 9/1973 | Boenning et al. |
| 4,917,486 A | 4/1990 | Raven et al. |
| 5,734,459 A * | 3/1998 | Chang ........................ 351/242 |
| 5,997,141 A | 12/1999 | Heacock |
| 6,183,086 B1 * | 2/2001 | Neubert ...................... 351/221 |

FOREIGN PATENT DOCUMENTS

| | | |
|---|---|---|
| EP | 0 960 610 A1 | 12/1999 |
| JP | 60-114233 | 6/1985 |
| JP | 8-38430 | 2/1996 |
| JP | 10033481 | 2/1998 |
| WO | WO 96/05693 | 2/1996 |
| WO | WO 00/12001 | 3/2000 |
| WO | WO 00/54655 | 9/2000 |

* cited by examiner

Primary Examiner—George Manuel
(74) Attorney, Agent, or Firm—Oliff & Berridge, PLC

(57) ABSTRACT

An opthalmic apparatus includes an illumination optical system for illuminating an eye of a patient, the illumination optical system including a plurality of LEDs which are illumination light sources for emitting beams of light of wavelengths in different regions and a composing optical system for composing optical paths of the beams of light emitted from the LEDs, an observation optical system for observing the patient's eye, and a light quantity control section capable of controlling an illumination light quantity of each of the LEDs to produce substantially white illumination light.

8 Claims, 6 Drawing Sheets

OPHTHALMIC APPARATUS

BACKGROUND OF THE INVENTION

1. Field of the Invention

The present invention relates to an ophthalmic apparatus for performing observation or treatment by illuminating an eye of a patient.

2. Description of Related Art

As an ophthalmic apparatus for observing a patient's eye, there is known a slit lamp for projecting slit-shaped illumination light on the patient's eye, thereby allowing observation through an observation optical system, or a laser treatment apparatus constructed by a combination of the slit lamp and a laser irradiation device.

These ophthalmic apparatus each cause an illumination light source provided inside of the apparatus to project illumination light on the patient's eye to thereby performing observation and treatment. A tungsten lamp, a halogen lamp or the like is generally used for the illumination light source.

However, an illumination light source using a lamp is short in service life. Thus, such illumination light source requires frequent replacement, which is cumbersome and imposes burden on operators or the like. In addition, the lamp has a large heat rate during illumination, and may have a thermal effect on its periphery. It is therefore required to pay attention to a material or an installation position, etc. of the periphery of the illumination light source during design.

The slip lamp is provided with a mechanism to insert/remove a wavelength selection filter for enabling fluorescent observation or the like into/from an illumination optical path. This may increase complexity in configuration of the apparatus.

In many cases, a laser treatment apparatus for performing photocoagulation or the like is provided with a protective filter disposed in an observation optical path in order to protect an operator's eye from a laser beam for treatment reflected from the patient's eye or the like. However, in the case of observation through a protective filter for cutting a visible treatment laser beam, an observation image looks more colorful than that in the case where no protective filter is provided, has strangeness, and makes it difficult to ensure observation.

SUMMARY OF THE INVENTION

The present invention has been made in view of the above mentioned technical problems. It is an object of the present invention to provide an ophthalmic apparatus provided with an illumination light source which is easy-to-handle and arranged in simplified configuration.

Another object of the present invention is providing an ophthalmic apparatus capable of facilitating observation even in the presence of a protective filter during laser treatment.

In order to solve the foregoing problems, the present invention is characterized by comprising the following constituent elements.

According to a first aspect of the present invention, there is provided an ophthalmic apparatus including: an illumination optical system for illuminating an eye of a patient, the illumination optical system including a plurality of LEDs which are illumination light sources for emitting beams of light of wavelengths in different regions and a composing optical system for composing optical paths of the beams of light emitted from the LEDs; an observation optical system for observing the patient's eye; and a light quantity control section capable of controlling an illumination light quantity of each of the LEDs to produce substantially white illumination light.

According to another aspect of the present invention, there is provided an ophthalmic apparatus including: an illumination optical system for illuminating an eye of a patient, the illumination optical system including a plurality of LEDs which are illumination light sources for emitting beams of substantially white light and a composing optical system for composing optical paths of the beams of light emitted from the LEDS; an observation optical system for observing the patient's eye; and a light quantity control section for controlling the light emission quantity of each of the LEDs.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENT

Figure 1:
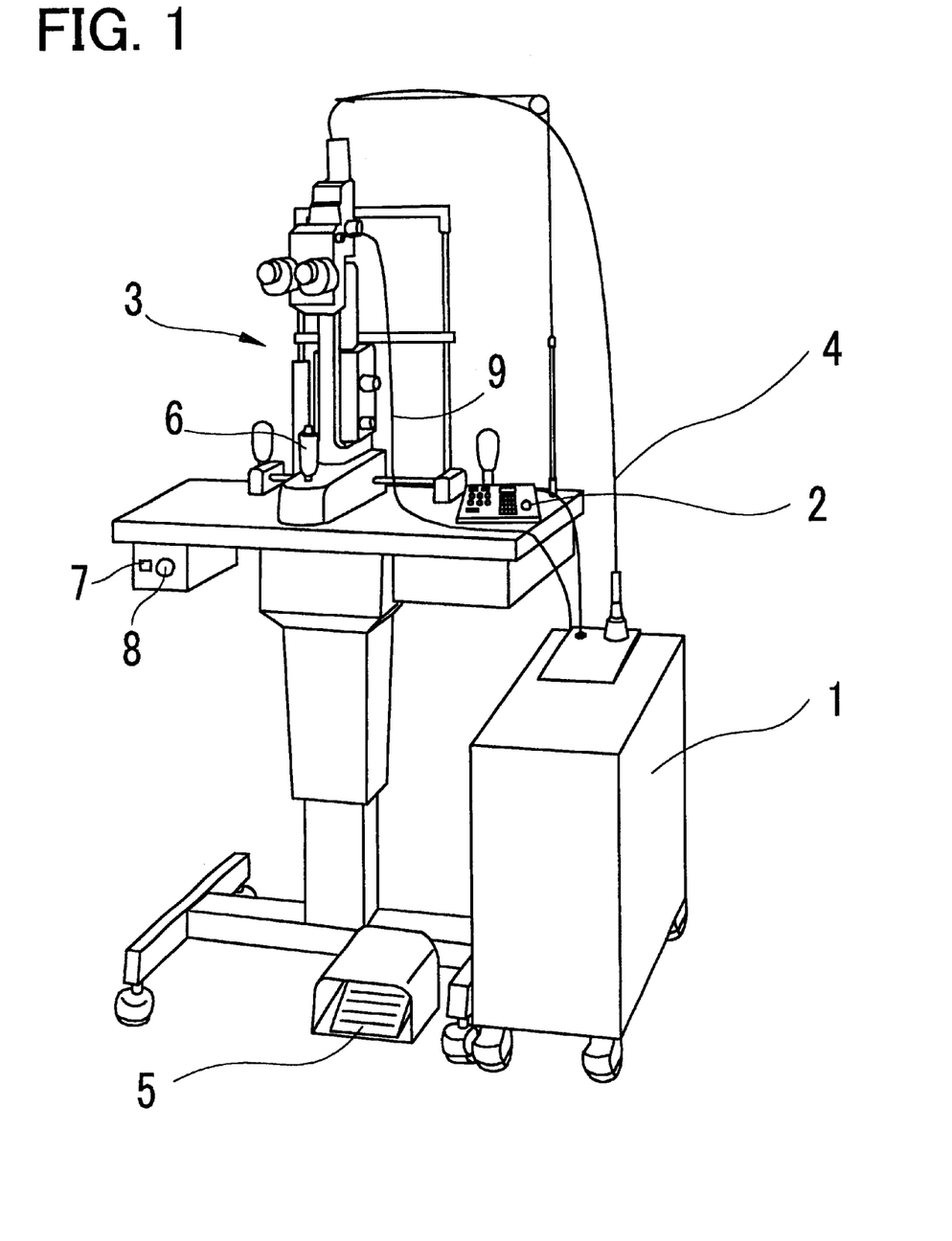
FIG. 1 is an external view showing a laser treatment apparatus in an embodiment according to the present invention.
Figure 2:
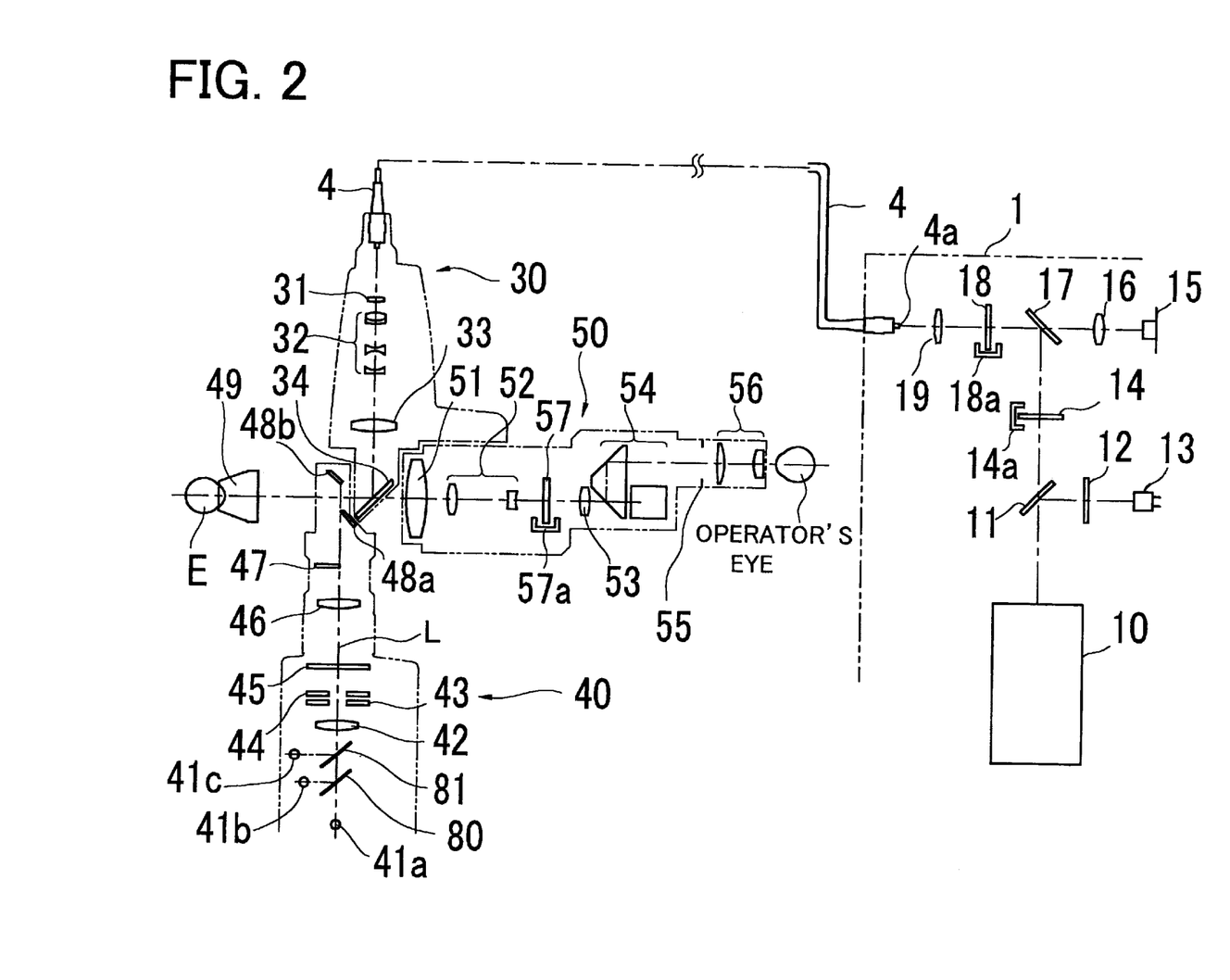
FIG. 2 is a schematic view showing an optical system of the apparatus.

A detailed description of a preferred embodiment of an ophthalmic apparatus embodying the present invention will now be given referring to the accompanying drawings. The present embodiment exemplifies a laser treatment apparatus as the ophthalmic apparatus according to the present invention. FIG. 1 is an external view showing a laser treatment apparatus for performing photocoagulation treatment by irradiating a laser light beam for treatment (hereinafter, merely referred to as a treatment beam) to the periphery an affected part of a patient's eye. FIG. 2 is a schematic view showing an opitical system of the apparatus.

Reference numeral 1 denotes a main body of the laser treatment apparatus. Reference numeral 2 is a control board for setting and inputting irradiation output conditions of the treatment beam. Reference numeral 3 denotes a slit lamp delivery comprising a laser irradiation optical system 30, an illumination optical system 40, and an observation optical system 50. Reference numeral 4 is a fiber cable for delivering the treatment beam or an aiming laser light beam (hereinafter, merely referred to as an aiming beam) from the main body 1 to the slit lamp delivery 3. Reference numeral 5 is a foot switch for generating a trigger signal to start laser irradiation. Reference numeral 6 is a joystick for moving the slit lamp delivery 3.

Reference numeral 7 denotes a switch for lighting LEDs 41a–41c that constitute an illumination light source incorporated in the slit lamp delivery 3. Reference numeral 8 denotes a light adjusting knob for adjusting an illumination light quantity. Reference numeral 9 is a cable connecting between the slit lamp delivery 3 and a control section 60 (see FIG. 3) on the side of the main body 1. The cable 9 is used for transmitting and receiving a command signal to insert/remove a protective filter 57 with respect to an optical path of the observation optical system 50 (hereinafter, referred to as an observation optical path) or a detection signal indicating the insertion or removal of the filter 57 (i.e. the presence or absence of the filter 57 in the observation optical path). The cable 9 is also used to transmit whether the toot switch 5 is active or inactive to the slit lamp delivery 3.

Reference numeral 10 denotes a laser source for emitting a treatment beam. In the present embodiment, as the laser source 10, an Nd:YAG laser capable of oscillating a fundamental wave of 1064 nm is used to generate a green light of 532 nm (linearly polarized light), which is double the fundamental wave. Reference numeral 11 is a beam splitter having the property of transmitting most part of the treatment beam emitted from the laser source 10 while reflecting a part of the beam. The part of the treatment beam reflected by the beam splitter 11 enters an output sensor 13 through a diffusing plate 12 for detecting the output value of the treatment beam.

Reference numeral 14 is a safety shutter. When the foot switch 5 is depressed, issuing a command for laser irradiation (i.e. generating a trigger signal), the safety shutter 14 is removed from the optical path, thus enabling the passing of the treatment beam. In case where an abnormality occurs, the safety shutter 14 is inserted into the optical path to thereby intercept the laser beam. The opening and closing of this shutter 14 is detected by means of a shutter sensor 14a.

Reference numeral 15 denotes a laser light source for emitting an aiming beam. In the present embodiment, there is used a semiconductor laser source capable of emitting a red aiming beam of 630 nm. The aiming beam emitted from the light source 15 passes through a collimator lens 16 and is made coaxial to the treatment beam by means of a dichroic mirror 17.

Reference numeral 18 is a second safety shutter. The opening and closing of this shutter 18 is detected by a shutter sensor 18a. Reference numeral 19 denotes a focusing lens for focusing the laser beams (the treatment beam and the aiming beam) to an incident end face 4a to enter the fiber 4. The laser beams are delivered through the fiber 4 to the irradiation optical system 30 of the slit lamp delivery 3.

The irradiation optical system 30 comprises a collimator lens 31, a variable magnification lens group 32, an objective lens 33, and a driving mirror 34. An operator can operate a manipulator (not shown), whereby to change the reflection angle of the driving mirror 34 to fine adjust a laser irradiation position.

Reference numeral 40 denotes an illumination optical system. Reference numerals 41a, 41b, and 41c each denote an LED used as an illumination light source. The LEDs 41a–41c emit beams of illumination light in wavelength regions for red (R), green (G), and blue (B), respectively, that are the primary colors of light.

Figure 4:
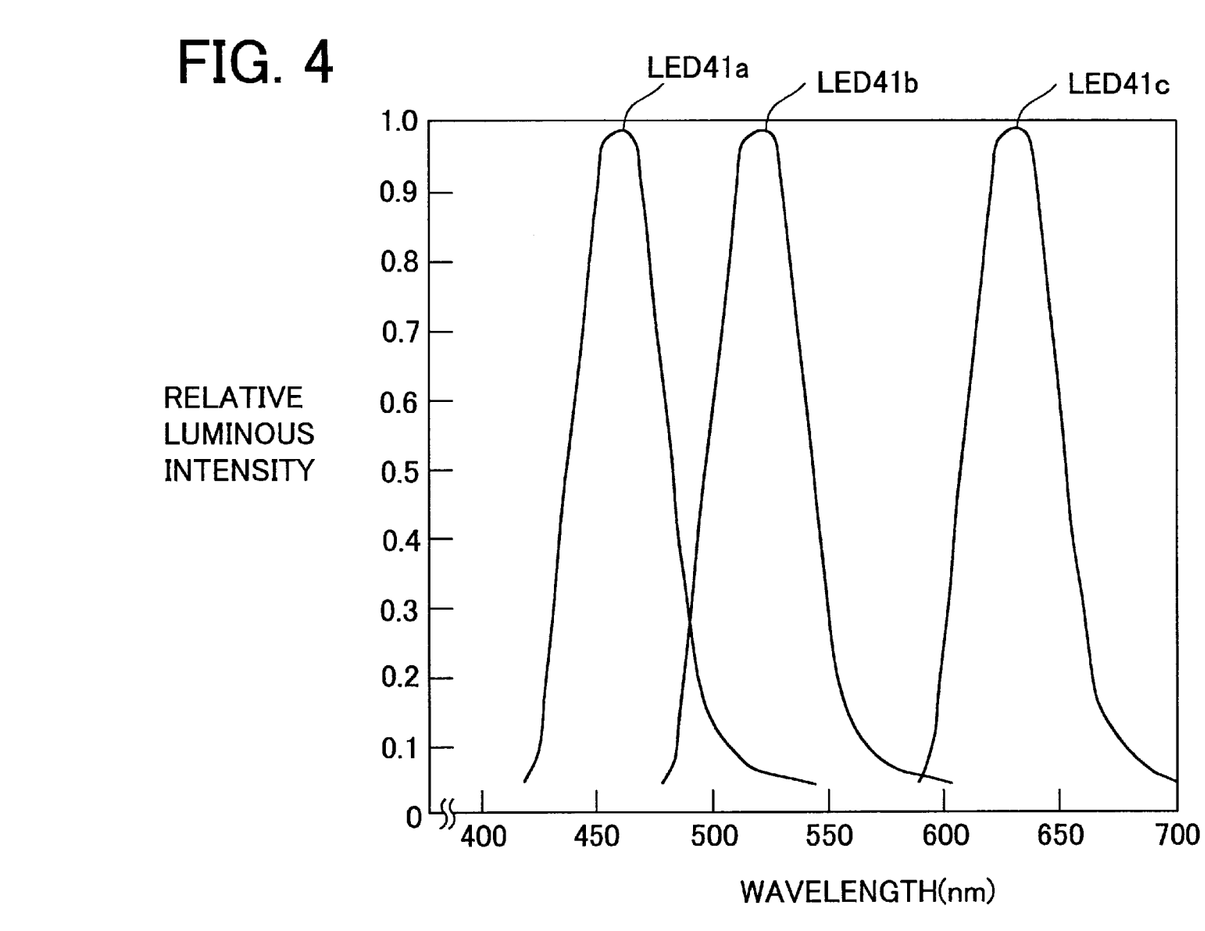
FIG. 4 is a view showing wavelength characteristics of each LED.

The wavelength characteristics of each of the LEDs 41a, 41b, and 41c are shown in FIG. 4. The LED 41a emits illumination light of the blue wavelength region of which a peak light emission wavelength is close to 460 nm, and the blue illumination light is allowed to pass through dichroic mirrors 80 and 81 disposed on an optical axis L. The LED 41b emits illumination light of a green wavelength region of which a peak light emission wavelength is close to 520 nm. The green illumination light is reflected by the dichroic mirror 80 to be composed with the blue illumination light. Then, the resultant light is allowed to pass through the dichroic mirror 81. The LED 41c emits illumination light of a red wavelength region of which a peak light emission wavelength is close to 630 nm. The red illumination light is reflected by the dichroic mirror 81 to be composed with the beams of blue and green illumination light.

In the present embodiment, although the dichroic mirrors 80 and 81 are used to make the beams of illumination light (red, green, and blue light beams) coaxial to each other (composed with each other), the present invention is not limited to such dichroic mirror. A beam combining device such as half mirror, polarizing plate, or prism may be used.

The beams of visible illumination light emitted from the LEDs 41a–41c and made coaxial (composed with each other) on the optical axis L are allowed to pass through a condenser lens 42. A height and a width of the resultant light are determined by a variable circular aperture plate 43 and a variable slit plate 44 respectively to be formed into a slit-shaped luminous flux. Then, the slit-shaped illumination light is allowed to pass through a projection lens 46 and then reflected by dividing mirrors 48a and 48b toward the patient's eye E. The light thus illuminates the eye E through a contact lens 49. Reference numeral 47 is a correction lens, and reference numeral 45 is a wavelength selection filter to be inserted into or removed from the optical path of the illumination optical system 40 (hereinafter, referred to as illumination optical path).

Figure 5:
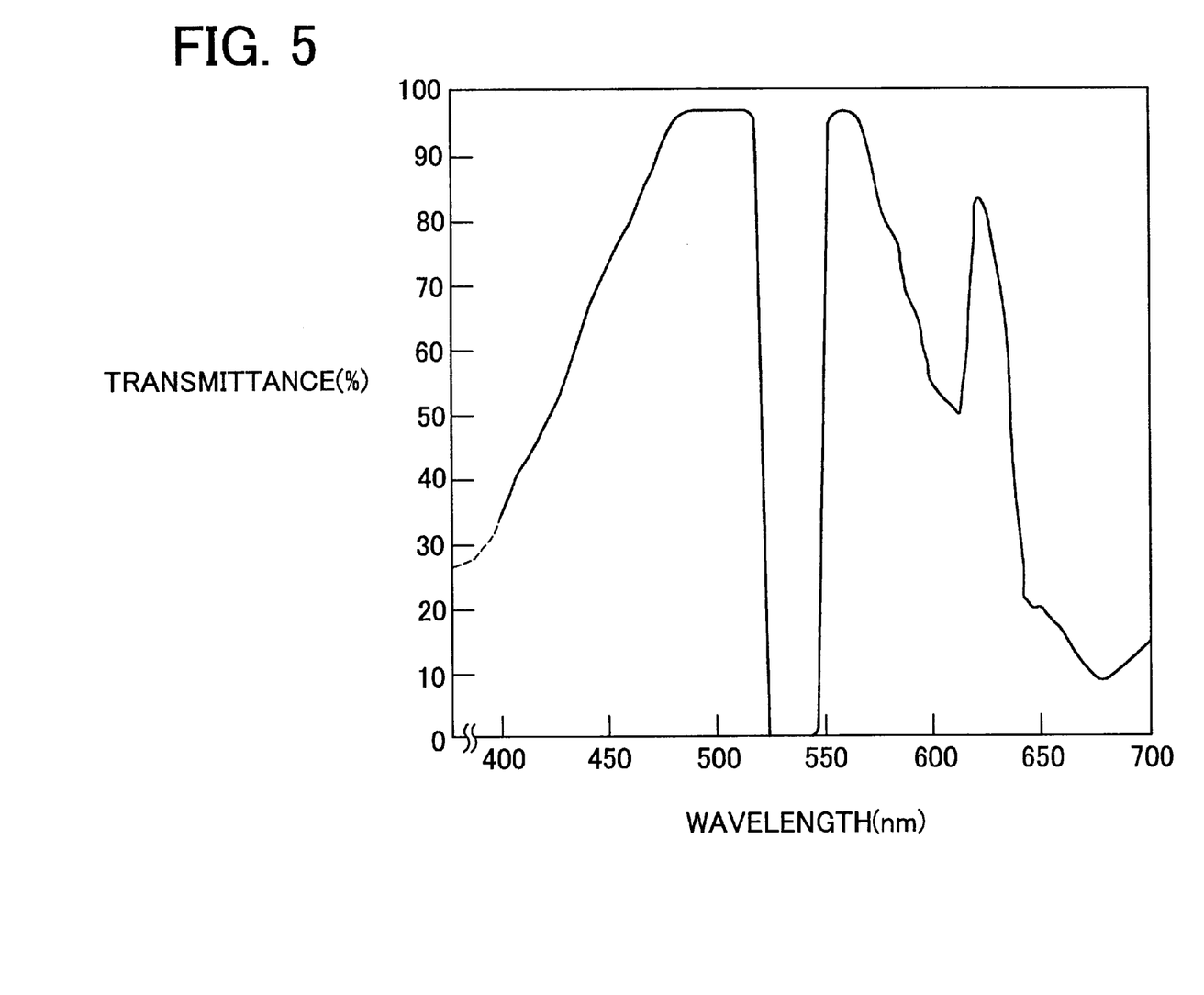
FIG. 5 is a view showing wavelength transmission characteristics of a protective filter.

An observation optical system 50 comprises: an objective lens 51 shared between the left and right observation optical paths; a variable magnification lens 52; an image forming lens 53; an erect prism 54; a field diaphragm 55; eyepiece lenses 56; and the protective filter 57; the elements 53–57 being disposed in the left and right observation optical paths, respectively. FIG. 5 is a view showing wavelength transmission characteristics of the filter 57. The filter 57 used in the present embodiment has the property of cutting 99% or more of light of a narrow bandwidth wavelength region (520 nm–540 nm), the center of which is 532 nm of the treatment beam, while allowing most of light of the visible wavelength region.

The filter 57 is arranged to be insertable into or removable from the observation optical path by means of a movement mechanism constructed of a motor or the like (not shown). The insertion and removal of the filter 57 with respect to the observation optical path is effected based on the presence or absence of the trigger signal from the foot switch 5. The condition of the filter 57, or the presence or absence of the filter 57 in the observation optical path, is detected by means of a sensor 57a.

Figure 3:
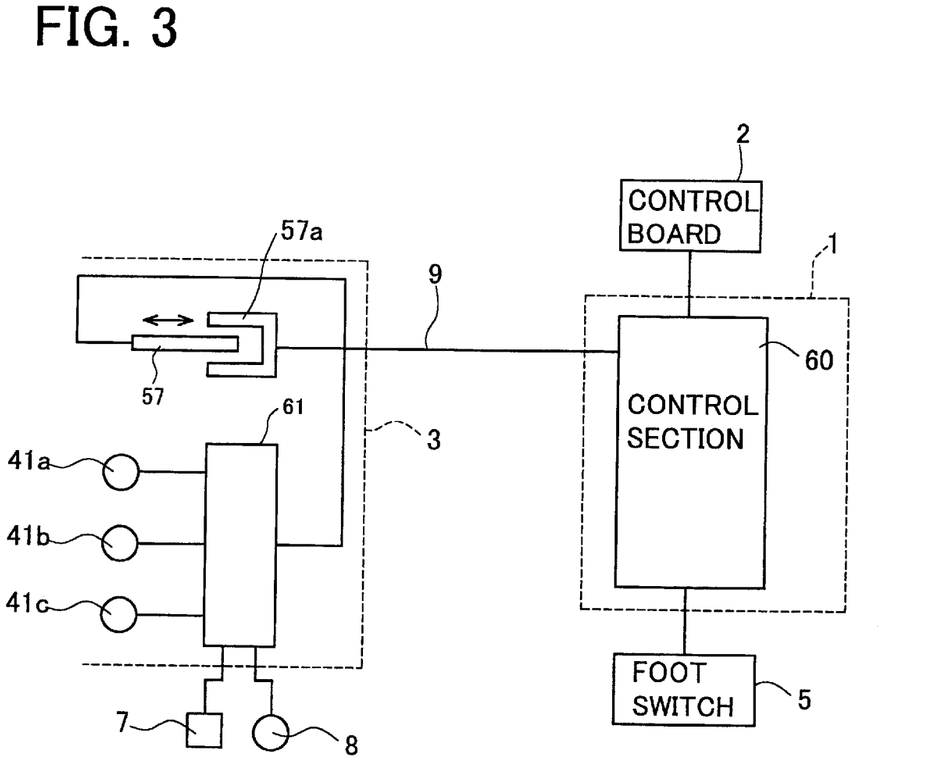
FIG. 3 is a block diagram schematically showing a control system of the apparatus.

Operation of the apparatus constructed as above will be described with reference to a block diagram schematically showing a control system shown in FIG. 3.

An operator turns on the LEDs 41a–41c by means of the switch 7. At this time, the light quantity of each of the illumination light beams emitted from the LEDs 41a–41c is controlled in advance by a light quantity control section 61 so that white illumination light is produced after three luminous fluxes (red, green, and blue) have been composed. To be more specific, the light quantities of the LEDs 41a, 41b, and 41c are each controlled so that the light quantities have the following ratio; LED 41a: LED 41b: LED 41c (B:G:R)=0.5:0.6:1.0.

As a result, the illumination light beams emitted from the LEDs 41a–41c are changed into a substantially white illumination light after they are composed; the white illumination light illuminates the patient's eye E; and the operator can obtain an observation image (observation visual field) in close to a natural color. It in to be noted that the light quantity ratio is not limited to the above, another ratio may be adopted if only the color of the illumination light produced by composition is within a region of white light.

Even when the light quantity of illumination light projected to the patient's eye E is changed by using the light adjusting knob 8, the light quantity is increased or decreased by the light quantity control section 61 without changing the ratio of the light emission quantities of the LEDs 41a–41c. This makes it possible to maintain the illumination light after composed in a substantially white color.

Since the LED is used as the illumination light source in the present embodiment, heating quantity can be reduced, thus eliminating the need to consider a thermal effect caused by the illumination light from the LED. Such each LED has its long service life, and may not be frequently replaced.

The illumination light beams from the LEDs 41a, 41b, and 41c are composed by the dichroic mirrors 80 and 81, whereby substantially white illumination light is produced as described above, which illuminates the patient's eye E through the illumination optical system 40. The operator can observe through the observation optical system 50 the fundus of the patient's eye E illuminated by the white illumination light.

Next, the aiming laser source 15 is lit by a switch (not shown) on the control board 2. Upon setting of the emission of the aiming beam, the control section 60 causes the shutter 18 to be removed from the optical path.

The operator operates the joystick 6 and a manipulator (not shown) while observing the aiming beam irradiated to the eye fundus, and performs alignment with respect to an affected part of the eye fundus. The operator sets irradiation conditions such as the irradiation power or irradiation time of the treatment beam by using various switches on the control board 2. When the laser irradiation is ready, a READY status is established such that the irradiation of the treatment beam is enabled. Then, the operator operates the manipulator (not shown) to make fine adjustment for alignment with the affected part. After completion of the alignment, the operator depresses the foot switch 5 to start the laser irradiation. Upon receipt of the trigger signal from the foot switch 5, the control section 60 generates a command signal to insert the filter 57 into the observation optical path. The sensor 57a detects that the filter 57 is inserted into the observation optical path and transmits the detection signal to the light quantity control section 61.

Upon receipt of the detection signal from the sensor 57a, the light quantity control section 61 changes the ratio of the light quantities of the LEDs 41a–41c in synchronization with the insertion of the filter 57 into the observation optical path. A change quantity of this light quantity ratio is preset so that the light densities of R, G, and B that pass through the filter 57 are close to those obtained in the absence of the filter 57 in the observation optical path.

The above change of the light quantity ratio by the light quantity control section 61 is effected for the following reason.

That is, when the reflection light from the patient's eye E passes through the filter 57, light of wavelengths in a range of 520 nm to 540 nm is cut by the filter 57 in order to cut the treatment beam. In association with this, the density of the green light is reduced. In this case, the ratio of the light quantities of the light beams passed through the filter 57 becomes the following relation; B:G:R=0.8:0.3:1.0. Consequently, the entire observation image obtained during observation through the filter 57 is more colorful (purplish) than that obtained in the absence of the filter 57.

To compensate for the density of the green light cut by the filter 57, the density of light of a green wavelength region which is allowed to pass through the filter 57 is relatively increased.

The ratio of respective light quantities of the LEDs 41a–41c is changed, for example, by increasing the light quantity of LED 41b, while decreasing those of the LEDs 41a and 41c, so that the light quantity ratio of the light beams passed through the filter 57 is adjusted to the relation; B:G:R=0.5:0.6:1.0. In this case, the ratio of respective actual light quantities of the LEDs shows the following relation; LED 41a: LED 41b:LED 41c (B:G:R)=0.3:1.0:0.9. In this manner, the colored degree of an observation image is lowered, and an observation image produced in the presence of the filter 57 in the observation optical path can be given the tone close to the observation image produced in the absence of the filter 57 therein.

Relative control of the light quantity ratio of the LEDs 41a–41c may be experimentally determined so that the tones of the observation images in the presence and the absence of the filter 57 are as identical to each other as possible.

When confirmed the insertion of the filter 57 into the observation optical path through the sensor 57a (when received the detection signal representative of the presence of the filter 57 from the sensor 57a), the control section 60 causes the shutter 14 to be removed from the optical path and the laser source 10 to emit the treatment beam. The treatment beam is delivered through the optical system in the main body 1, the fiber 4, and the irradiation optical system 30, to irradiate the affected part of the patient's eye E.

Even if the filter 57 is inserted during laser irradiation, i.e., in the observation optical path, the observation image is obtained in a color state close to a natural color which is obtained during the observation in the absence of the filter 57. Thus, the state of the affected part or treatment result can be observed without any strangeness. Further, even when the filter 57 is placed in the observation optical path for a long time for continuous laser irradiation, there is no need to remove the filter 57 in the middle of treatment because of a low visibility in order to allow the operator to check the treatment state without the filter 57. The light quantity control mentioned above is therefore particularly effective for the continuous laser irradiation.

When the operator stops depressing the foot switch 5, no trigger signal is generated therefrom. In response to no signal from the foot switch 5, the control section 60 stops the laser emission from the laser source 10 and removes the filter 57 from the observation optical path. In association with the detection signal from the sensor 57a that has detected the removal of the filter 57, the light quantity control section 61 resets the light quantity ratio of the LEDs 41a–41c to the original light quantity ratio used before the insertion of the filter 57. In this manner, even after the filter 57 is removed from the observation optical path, there can be obtained an observation image with substantially the same tone as that obtained before the insertion of the filter 57 into the observation optical path.

The present invention may be embodied in other specific forms without departing from the essential characteristics thereof.

For instance, in the above embodiment, the light quantity ratio of the LEDs 41a–41c is changed in association with the detection signal from the sensor 57*a* representing the presence/absence of the filter 57 in the observation optical path. Alternatively, the ratio may be changed in response to the trigger signal from the foot switch 5.

The above embodiment has described an example of using three types of LEDs for emitting beams of illumination light of wavelengths in regions for R, G, and B. However, if those three types of LEDs are insufficient to produce a substantially white illumination light, the types of LEDs for emitting beams of illumination light of wavelengths in different regions from the above three regions may be further increased so that the substantially white illumination light is easily obtained. In the case where the illumination light quantity is insufficient, the number of LEDs may be increased for each color.

Furthermore, although the present embodiment describes an example of a laser treatment apparatus, the present invention is, of course, applicable to only a slit lamp. In this case, there is conveniently provided selection keys 70*a*, 70*b*, and 70*c* for selectively lighting the LEDs 41*a*, 41*b*, and 41*c* for B, G, and R light or individually adjusting the light quantity of each of the 41*a*–41*c* (see FIG. 6). For example, in the fluorescent observation using fluorescein eyewash, the LED 41*a* is lit so that the patient's eye E is illuminated by blue illumination light capable of exciting fluorescein.

Figure 6:
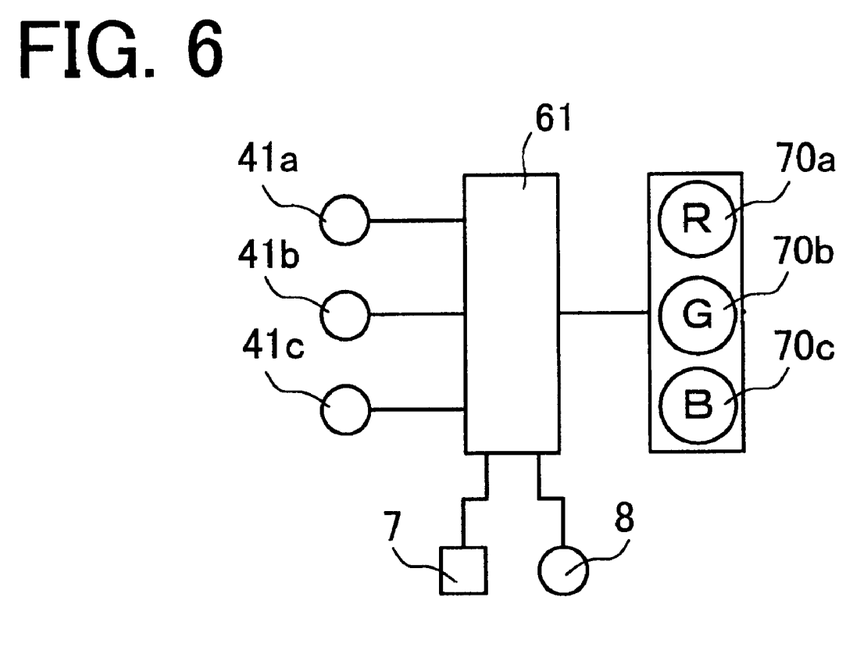
FIG. 6 is a block diagram schematically showing a mechanism for selectively lighting LEDs.

In the observation of blood vessels of conjunctiva or the like, the LED 41*b* for emitting green illumination light is lit without illumination by red illumination light, thereby facilitating the observation. This makes it also possible to eliminate a filter mechanism for selecting wavelengths from the illumination optical system 40. In such a case, an LED for emitting light of wavelengths required for the fluorescence observation or the like may be provided in advance as an LED for an illumination light source.

Alternatively, the light quantity of red illumination light may be reduced or the light quantity of green illumination light or blue illumination light may be increased in order to finely adjust the illumination light to an easy-to-observe color according to the color of an observation site.

The lighting of the LEDs 41*a*–41*c* or the light quantity control is effected by the light quantity control section 61 connected to the selection keys 70*a*–70*c*. In the case where the entire illumination light quantity is controlled without changing the light quantity ratio of the colors, the knob 8 is used. Alternatively, an LED for emitting illumination light of wavelengths according to types of the fluorescence observation or the like may be provided separately from the LED for an illumination light source.

Furthermore, even if only one type of a white-emitting LED is used without use of three types (R, G, and B) of LEDs, the use of such white-emitting LED is very effective in heat generation and service life in comparison with a conventional halogen lamp or tungsten lamp.

As has been described above, according to the present invention, the apparatus with an illumination light source which is easy-to-handle and a simplified configuration can be achieved. Furthermore, in the laser treatment, the affected part of the patient's eye can be easily observed even in the presence of the protective filter in the optical path of the observation optical system.

What is claimed is:

1. An ophthalmic apparatus including:
   an illumination optical system for illuminating an eye of a patient, the illumination optical system including a plurality of LEDs which are illumination light sources for emitting beams of light of wavelengths in different regions and a composing optical system for composing optical paths of the beams of light emitted from the LEDs;
   an observation optical system for observing the patient's eye;
   an irradiation optical system for irradiating a visible laser beam for treatment to the patient's eye;
   a protective filter for preventing the treatment laser beam from entering an eye of an observer, the protective filter being disposed insertably into and removably from an observation optical path of the observation optical system; and
   a light quantity control section capable of controlling an illumination light quantity of each of the LEDs to produce substantially white illumination light,
   wherein the light quantity control section changes a ratio of the light emission quantities of the LEDs in association with at least one of insertion and removal of the protective filter.

2. The ophthalmic apparatus according to claim 1 further including a sensor for detecting a presence or absence of the protective filter in the observation optical path,
   wherein the light quantity control section changes the ratio of the light emission quantities of the LEDs based on a detection result by the sensor.

3. The ophthalmic apparatus according to claim 1, wherein the light quantity control section changes the ratio of the light emission quantities of the LEDs so that an observation image obtained in a presence of the protective filter in the observation optical path has a substantially same tone as an observation image obtained in an absence of the protective filter in the observation optical path.

4. The ophthalmic apparatus according to claim 1, wherein, when the protective filter is inserted into the observation optical path, the light quantity control section relatively increases the light emission quantity of an LED for emitting light of a color corresponding to a wavelength region to be cut by the protective filter.

5. The ophthalmic apparatus according to claim 1, wherein the plurality of LEDs include an LED for emitting red light, an LED for emitting green light, and an LED for emitting blue light.

6. The ophthalmic apparatus according to claim 1, further including a selection key for selectively causing the plurality of LEDS to emit light,
   wherein the light quantity control section is capable of controlling the light emission quantity of each of the LEDs based on selection by means of the selection key.

7. The ophthalmic apparatus according to claim 1, further including a light adjusting knob or a light adjusting key for changing the light quantity of substantially white illumination light,
   wherein the light quantity control section changes the light emission quantity of each of the LEDs based on adjustment by means of the light adjusting knob or key while the ratio of the light emission quantities of the LEDs is kept unchanged.

8. An ophthalmic apparatus including:
   an illumination optical system for illuminating an eye of a patient, the illumination optical system including a plurality of LEDs which are illumination light sources for emitting beams of substantially white light and a composing optical system for composing optical paths of the beams of the light emitted from the LEDs;
   an observation optical system for observing the patient's eye;
   an irradiation optical system for irradiating a visible laser beam for treatment to the patient's eye;
   a protective filter for preventing the treatment laser beam from entering an eye of an observer, the protective filter being disposed insertably into and removably from an observation optical path of the observation optical system; and a light quantity control section for controlling the light emission quantity of each of the LEDs, wherein the light quantity control section changes a ratio of the light emission quantities of the LEDs in association with at least one of insertion and removal of the protective filter.

* * * * *